(12) United States Patent
Sokolinsky et al.

(10) Patent No.: US 7,223,382 B2
(45) Date of Patent: May 29, 2007

(54) COSMETIC COMPOSITIONS CONTAINING ROSEMARY EXTRACT AND DHA

(75) Inventors: Marina Sokolinsky, Smithtown, NY (US); Asira Ostrovskaya, Bayside, NY (US); Peter A. Landa, Springfield, NJ (US); Daniel H. Maes, Huntington, NY (US)

(73) Assignee: E-L Management Corporation, Melville, NY (US)

( * ) Notice: Subject to any disclaimer, the term of this patent is extended or adjusted under 35 U.S.C. 154(b) by 482 days.

(21) Appl. No.: 10/451,565

(22) PCT Filed: May 29, 2002

(86) PCT No.: PCT/US02/16766

§ 371 (c)(1),
(2), (4) Date: Jun. 20, 2003

(87) PCT Pub. No.: WO02/096371

PCT Pub. Date: Dec. 5, 2002

(65) Prior Publication Data

US 2004/0042979 A1   Mar. 4, 2004

(51) Int. Cl.
*A61Q 17/04* (2006.01)
*A61Q 15/00* (2006.01)
*A61Q 19/00* (2006.01)
*A61K 8/02* (2006.01)

(52) U.S. Cl. .............. 424/59; 424/60; 424/65; 424/400; 424/401

(58) Field of Classification Search .............. 424/59, 424/60, 65, 400, 401
See application file for complete search history.

(56) References Cited

U.S. PATENT DOCUMENTS 5,827,506 A * 10/1998 McShane et al. ............ 424/59
6,294,161 B1    9/2001 Hiramoto et al.

FOREIGN PATENT DOCUMENTS

| FR | 2 712 804 A | 6/1995 |
| JP | 57-204278 | 12/1982 |
| JP | 59-103665 A | 6/1984 |
| WO | WO94/22419 | 10/1994 |

* cited by examiner

*Primary Examiner*—Shelley A. Dodson
(74) *Attorney, Agent, or Firm*—Cynthia Miller

(57) ABSTRACT

The present invention relates to a topical composition comprising a malodor-reducing effective amount of a rosemary extract, or active fraction thereof, in combination with a self-tanning effective amount of DHA. The invention also provides a method of reducing the potential for malodor generation of a DHA composition comprising adding to the composition an effective amount of rosemary extract or active fraction thereof.

18 Claims, No Drawings

COSMETIC COMPOSITIONS CONTAINING ROSEMARY EXTRACT AND DHA

FIELD OF THE INVENTION

The invention relates to cosmetic compositions. More specifically, the invention relates to self-tanning cosmetic compositions.

BACKGROUND OF THE INVENTION

With sun exposure being recognized as a significant health risk, the desirability of sitting for hours to develop a deep tan has diminished considerably in recent years. However, the desire to have that bronze glow has not diminished in a large portion of the population. The solution for most prudent consumers is the use of self-tanning products. These products typically employ the compound dihydroxyacetone (DHA), which interacts with the proteins on the skin to produce a brown color approximating a sun-derived tan. In the early days of self-tanners, there were a number of problems which prevented widespread acceptance, the primary one being the unnatural orange color that would develop on some users. However, self-tanners have improved tremendously in recent years, and most products currently available produce natural and fairly long-lasting color on the user. There is one remaining issue with self-tanners that continues to reduce their acceptability to the consumer: after application, many users detect a malodor that lingers for up to 24 hours. The unpleasant odor apparently arises as a result of compounds generated on the skin upon application of the self-tanner. The only solution known to date is the incorporation of fragrance or oils that mask the odor to some extent; however, the addition of fragrance is not always an acceptable option to every product, and in any event does not address the root of the problem, i.e., neutralizing the compounds generated on the skin. To date, this problem continues to affect self-tanners, and therefore, may prevent their more frequent usage. The present invention now provides a solution for the odor generated upon application of the self-tanner to the skin.

SUMMARY OF THE INVENTION

The present invention relates to a cosmetic composition comprising DHA in combination with an effective amount of a rosemary extract or active component thereof. As used herein, the term "cosmetic composition" is intended to encompass any composition containing DHA intended for topical application to the skin, which may also include compositions that are used in therapeutic applications, for example, in conjunction with PUVA therapy.

The invention also relates to a method of preventing or reducing the generation of malodor on the skin resulting from application of a DHA-containing self-tanner, comprising applying to the skin a composition comprising DHA combined with an effective amount of rosemary extract.

DETAILED DESCRIPTION OF THE INVENTION

It has been unexpectedly discovered that the addition of rosemary extract to compositions containing DHA will prevent or reduce the typical malodor associated with the application of DHA compositions to the skin. Rosemary extract is a natural and known material extracted from the rosemary plant, and having established properties as an antioxidant. However, notwithstanding its known properties, in the present case, where the problem seems not to arise in degradation of the formula, but rather due to a reaction on the skin about which very little is known, it was quite unexpected that the rosemary extract performed so remarkably.

Rosemary extract is a generic term describing a number of different chemical compositions that may contain several different active components. Among the common components that are found in rosemary extract are carnosol, carnosic acid, methoxy carnosic acid, rosmarinic acid, rosmanol and rosmaridiphenol, in different proportions depending on the individual extract. Numerous rosemary extracts are available commercially, and any one can be used in the present invention. However, particularly preferred for use is the "Guardian" rosemary extract available from Earth Supplied Products. This extract contains, in a base of lecithin, acetylated hydrogenated vegetable glycerides and propylene glycol, an active rosemary extract, in an amount of from about 12-30%, containing a minimum of 5% phenolic diterpenes. In particular, the active portion contains a minimum of 50% carnosic acid, carnosol in an amount of 20-35%, and methoxy carnosic acid in an amount of from about 5-15%, with minor amounts of rosmanol, rosmarinic acid and rosmaridiphenol. It will be understood that the term "rosemary extract" as used herein shall encompass not only a rosemary extract per se, but also a composition to which the individual active components, such as are noted above, are added to the composition individually, or in individual combinations, from synthetic or natural sources, either from rosemary or from starting material other than rosemary, in amounts equivalent to those described in the use of the rosemary extract.

The active rosemary extract can be used in the DHA formulation in an amount of from about 0.001 to about 50% by weight of the total composition. However, the extract is extremely efficacious, requiring only small amounts to achieve reduction in odor, so the preferred range of use of the extract is about 0.1 to about 10% by weight of the composition. The extract can be added to any type of formulation in which DHA is ordinarily applied, for example, creams, lotions, sprays, sticks and the like, and may be aqueous, water and oil or anhydrous. The amount of DHA employed will be in line with the typical use of this material, which is generally in the range of from about 1-10%. Another unexpected result of the use of the rosemary extract is its lack of adverse effect on color development with DHA. DHA is a relatively unstable material, and is subject to alterations in its performance when in the presence of other incompatible materials. However, surprisingly, rosemary extract has no adverse effect on the color development, and in some cases even seemed to improve it.

The invention will be further understood by reference to the following non-limiting examples.

EXAMPLES

Example 1

Initial studies were performed to identify compounds which might assist in reducing the malodor associated with DHA application on the skin. A first attempt tested compounds generally known to have odor-reducing properties, namely, dipropylene glycol, zinc acetate, choline, and aloe vera gel. No consistent positive results were obtained with any of these compounds.

A secondary experiment was conducted on a new raw material: 'Guardian' Rosemary Extract produced by Earth Supplied Products. The influence of Rosemary Extract (RME) on odor formation on 14 panelists using aqueous solutions of DHA and Rosemary Extract was investigated. Color and odor were tested on the panelists to determine any differences in the reaction of DHA in the presence of Rosemary Extract.

Results and Discussions

I) Clinical Study: Applications of Aqueous Solutions of DHA alone and DHA with RME to the Skin In the presence of RME, significant odor improvement was observed on 13/14 panelists (0.25% RME). One panelist did not produce any malodor when DHA was applied. The improvement in odor was most evident at 24 hours after the application to the skin. Under these conditions we observed greater than 90% reduction in malodor formation.

When the color development was compared between test and control compositions, we observed that in the presence of RME, no difference in color was evident. (In some cases, the color development was slightly improved) Therefore, while using RME significantly reduced the malodor—there was no inhibition of the DHA color reaction as was seen previously with other ingredients tested.

Example 2

The following illustrates a composition, a water and oil emulsion, of the invention:

| Material | Weight % |
|---|---|
| Cyclomethicone | 11.00 |
| Cetyl Dimethicone copolyol | 1.00 |
| Cyclomethcone/PEG/PPG-18/18 dimethicone | 5.00 |
| Tocopheryl acetate | 0.20 |
| Polysilicone 7/cyclomethicone | 1.50 |
| Fragrance | 0.40 |
| Deionized water | QS |
| DHA | 4.00 |
| Glycerin | 8.00 |
| Sodium chloride | 0.80 |
| Lactic acid | 0.50 |
| Pantethine | 0.02 |
| Cyclomethicone | 2.00 |
| Black Iron oxide | 0.02 |
| Iron oxide/alumina | 0.38 |
| Mica/titanium dioxide/iron oxides/dimethicone | 0.22 |
| Mica/iron oxides | 0.14 |
| Preservative | 0.50 |
| Rosemary extract | 0.25 |
| Cyclomethicone | 1.00 |
| Cyclomethicone/dimethicone/vinyl dimethicone crosspolymer | 3.50 |

What we claim is:

1. A cosmetic self-tanning composition comprising a self-tanning effective amount of DHA and active rosemary extract, or active fraction thereof, in an amount sufficient to reduce the malodor generated on the skin upon application of the self-tanning composition, wherein the amount of the active rosemary extract, or active fraction thereof, comprises from about 0.1% to about 10% by weight of the composition.

2. The composition of claim 1 comprising from about 1 to about 10% of DHA.

3. The composition of claim 1 in which the active rosemary extract, or active fraction thereof, comprises carnosol and carnosic acid.

4. The composition of claim 1 in which the active rosemary extract, or active fraction thereof, comprises at least about 50% by weight carnosic acid.

5. The composition of claim 1 in which the active rosemary extract, or active fraction thereof, comprises from about 20 to about 35% by weight carnosol.

6. The composition of claim 1 in which the active rosemary extract, or active fraction thereof, comprises from about 5 to about 15% by weight of methoxy carnosic acid.

7. A cosmetic composition comprising from about 1 to about 10% by weight of DHA, and active rosemary extract, or active fraction thereof, in an amount sufficient to reduce the malodor generated on the skin upon application of the composition, wherein the amount of the active rosemary extract, or active fraction thereof, comprises from about 0.1 to about 10% by weight of the composition.

8. The composition of claim 7 in which the active rosemary extract, or active fraction thereof, comprises at least about 50% by weight of carnosic acid.

9. The composition of claim 7 in which the active rosemary extract, or active fraction thereof, contains from about 20 to about 35% by weight of carnosol.

10. The composition of claim 9 in which the active rosemary extract, or active fraction thereof contains from about 5 to about 15% by weight of methoxy carnosic acid.

11. A method of formulating a DHA-containing composition which upon application to skin generates little or no malodor, comprising formulating the DHA-containing composition to include a malodor-reducing effective amount of active a rosemary extract, or active fraction thereof, wherein said effective amount is in the range of about 0.1% to about 10% by weight of the composition.

12. The method of claim 11 in which the active rosemary extract, or active fraction thereof, contains carnosic acid in an amount of at least about 50% by weight.

13. The method of claim 12 in which the active rosemary extract, or active fraction thereof, comprises from about 20 to about 35% by weight of carnosol.

14. The method of claim 13 in which the active rosemary extract, or active fraction thereof, comprises from about 5 to about 15% by weight methoxy carnosic acid.

15. A method of reducing or preventing the development of malodor on the skin associated with DHA-containing compositions, comprising applying to the skin the composition of claim 1.

16. A method of reducing or preventing the development of malodor on the skin associated with DHA-containing compositions, comprising applying to the skin the composition of claim 4.

17. A method of reducing or preventing the development of malodor on the skin associated with DHA-containing compositions, comprising applying to the skin the composition of claim 7.

18. A method of reducing or preventing the development of malodor on the skin associated with DHA-containing compositions, comprising applying to the skin the composition of claim 10.

* * * * *